(12) United States Patent
Bell

(10) Patent No.: US 9,106,713 B2
(45) Date of Patent: *Aug. 11, 2015

(54) DATA CAPTURING AND EXCHANGE METHOD AND SYSTEM

(71) Applicant: INOFILE LLC, Boise, ID (US)

(72) Inventor: Therasa Bell, Boise, ID (US)

(73) Assignee: INOFILE LLC, Boise, ID (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/156,237

(22) Filed: Jan. 15, 2014

(65) Prior Publication Data

US 2014/0250162 A1    Sep. 4, 2014

Related U.S. Application Data

(63) Continuation of application No. 13/844,006, filed on Mar. 15, 2013, now Pat. No. 8,682,993.

(60) Provisional application No. 61/771,474, filed on Mar. 1, 2013.

(51) Int. Cl.
  *G06F 15/16*  (2006.01)
  *H04L 29/08*  (2006.01)
  *G06F 19/00*  (2011.01)

(52) U.S. Cl.
  CPC ............. *H04L 67/32* (2013.01); *G06F 19/322* (2013.01)

(58) Field of Classification Search
  CPC ..................... H04L 67/32; G06F 19/322
  USPC .......................................... 709/206; 707/756
  See application file for complete search history.

(56) References Cited

U.S. PATENT DOCUMENTS

| | | | |
|---|---|---|---|
| 5,361,202 A | 11/1994 | Doue | |
| 5,572,422 A | 11/1996 | Nematbakhsh et al. | |
| 5,772,585 A | 6/1998 | Lavin et al. | |
| 5,823,948 A | 10/1998 | Ross, Jr. et al. | |
| 6,024,699 A | 2/2000 | Surwit et al. | |
| 6,347,329 B1 | 2/2002 | Evans | |
| 7,716,072 B1 | 5/2010 | Green, Jr. et al. | |
| 7,831,683 B2 | 11/2010 | Becker et al. | |
| 7,873,621 B1 | 1/2011 | Datar et al. | |
| 8,131,569 B2 | 3/2012 | Maresh et al. | |
| 8,145,582 B2 | 3/2012 | Angell et al. | |
| 8,166,389 B2 | 4/2012 | Czaplewski et al. | |
| 8,180,654 B2 | 5/2012 | Berkman et al. | |
| 8,468,033 B2 | 6/2013 | Gunn | |
| 2006/0287890 A1 | 12/2006 | Stead et al. | |
| 2009/0080408 A1 | 3/2009 | Natoli et al. | |

(Continued)

*Primary Examiner* — Krisna Lim
(74) *Attorney, Agent, or Firm* — Finnegan, Henderson, Farabow, Garrett & Dunner L.L.P.

(57) ABSTRACT

A method for a data capturing and exchange system. The data capturing and exchange system has a plurality of devices in a sub-network and a network server connected to the sub-network. The method includes capturing an unstructured data record of a document on a device, collecting metadata associated with the unstructured data record; determining a recipient for the unstructured data record in a health information exchange, and composing a data message containing the unstructured data record. The method also includes obtaining the composed data message containing the unstructured data record, packing the composed data message into a packed message containing a structured data record corresponding to the unstructured data record, and sending the packed message to the recipient in the HIE can receive and recognize the document.

23 Claims, 7 Drawing Sheets

(56) References Cited

U.S. PATENT DOCUMENTS

| | | |
|---|---|---|
| 2009/0132276 A1 | 5/2009 | Petera |
| 2009/0232398 A1 | 9/2009 | Martin et al. |
| 2010/0104200 A1 | 4/2010 | Baras et al. |
| 2010/0161352 A1 | 6/2010 | Lim et al. |
| 2010/0228559 A1 | 9/2010 | Boone |
| 2011/0137681 A1 | 6/2011 | Lim et al. |
| 2011/0145013 A1 | 6/2011 | McLaughlin |
| 2011/0202572 A1 | 8/2011 | Ho et al. |
| 2011/0246236 A1 | 10/2011 | Green, III et al. |
| 2012/0095923 A1 | 4/2012 | Herlitz |

DATA CAPTURING AND EXCHANGE METHOD AND SYSTEM

This application is a continuation of Application No. 13/844,006, filed Mar. 15, 2013 (now U.S. Patent 8,682,993), which claims priority to U.S. provisional application 61/771,474, filed Mar. 1, 2013, the entirety of which is incorporated herein by reference.

FIELD OF THE INVENTION

The present invention generally relates to data management technologies and, more particularly, to methods and systems for data capturing, structuring, and exchange.

BACKGROUND

The Internet and information technology make electronic data one of the most important aspects of running a business or even personal life. Data applications and systems are used in virtually all industries in many different ways, but data generated by different applications and systems must be managed, interpreted, and exchanged.

For example, healthcare organizations often use many different healthcare applications and systems to perform various services, both internal and external to the organizations. Much of the information these applications and systems collect, such as data and documents, must be uploaded and shared among internal and external systems, but that information is often unstructured.

A challenge many healthcare organizations currently face is that each day they generate a large amount of unstructured content, which may be in native form and stagnant and unusable by the other applications. For example, unless a human identifies scanned document, a digital photo, or electronic file, such as a PDF file, a healthcare application may be unable to identify the file, to whom it belongs to, or what to do with the file. Managing unstructured data in a healthcare organization is often expensive, time-consuming, and prone to error.

Another challenge healthcare organizations face is the difficulty to exchange unstructured files between entities or individuals on different networks, such as different healthcare organizations, patients, and vendors. As a result, the files are often printed and faxed to the recipients, which is not only time-consuming and expensive, but also leaves holes in the electronic patient record-keeping, which may cause security and patient safety risks.

The methods and systems below solve these and other problems.

BRIEF SUMMARY OF THE DISCLOSURE

Systems and methods consistent with this invention for data capture and exchange include devices in a sub-network and a network server connected to the sub-network. A method consistent with this invention includes capturing an unstructured data record of a document on a device, collecting metadata associated with the record; determining a recipient for the record in a health-information exchange, and composing a data message containing the unstructured data record. Such a method also includes obtaining the data message, packing it into a packed message containing a structured data record corresponding to the unstructured data record, and sending the packed message to the recipient in the HIE in a format that allows the recipient to receive and recognize the document.

A data capturing and exchange system consistent with this invention includes a sub-network with devices, and a network server connected to the sub-network to enable the devices to participate in a HIE based on structured data. Each device can be configured to capture an unstructured data record of a document on the device, collect metadata associated with the record, determine a recipient for the record, and compose a data message containing the unstructured data record. The network server is capable of obtaining the composed message, packing the composed data message into a packed message, and sending the packed message to the recipient in a format that allows the recipient to receive and recognize the document.

Another method consistent with this invention for a data capturing and exchange system with devices in a sub-network and a network server connected to the sub-network querying with a HIE about a data message destined to the sub-network, receiving a data message containing a structured data record and destined to the sub-network, and identifying a device in the sub-network for receiving the data message. The method also includes creating a general representation of the data message, indicating on an inbox of the device of the data messaging based on the general representation, receiving an unstructured data record corresponding to the data message, and acknowledging receipt of the unstructured data record to the network server.

BRIEF DESCRIPTION. OF THE DRAWINGS

DETAILED DESCRIPTION

Several exemplary embodiments are illustrated in the accompanying drawings. The same reference numbers in different drawings to refer to the same or similar parts.

Figure 1:
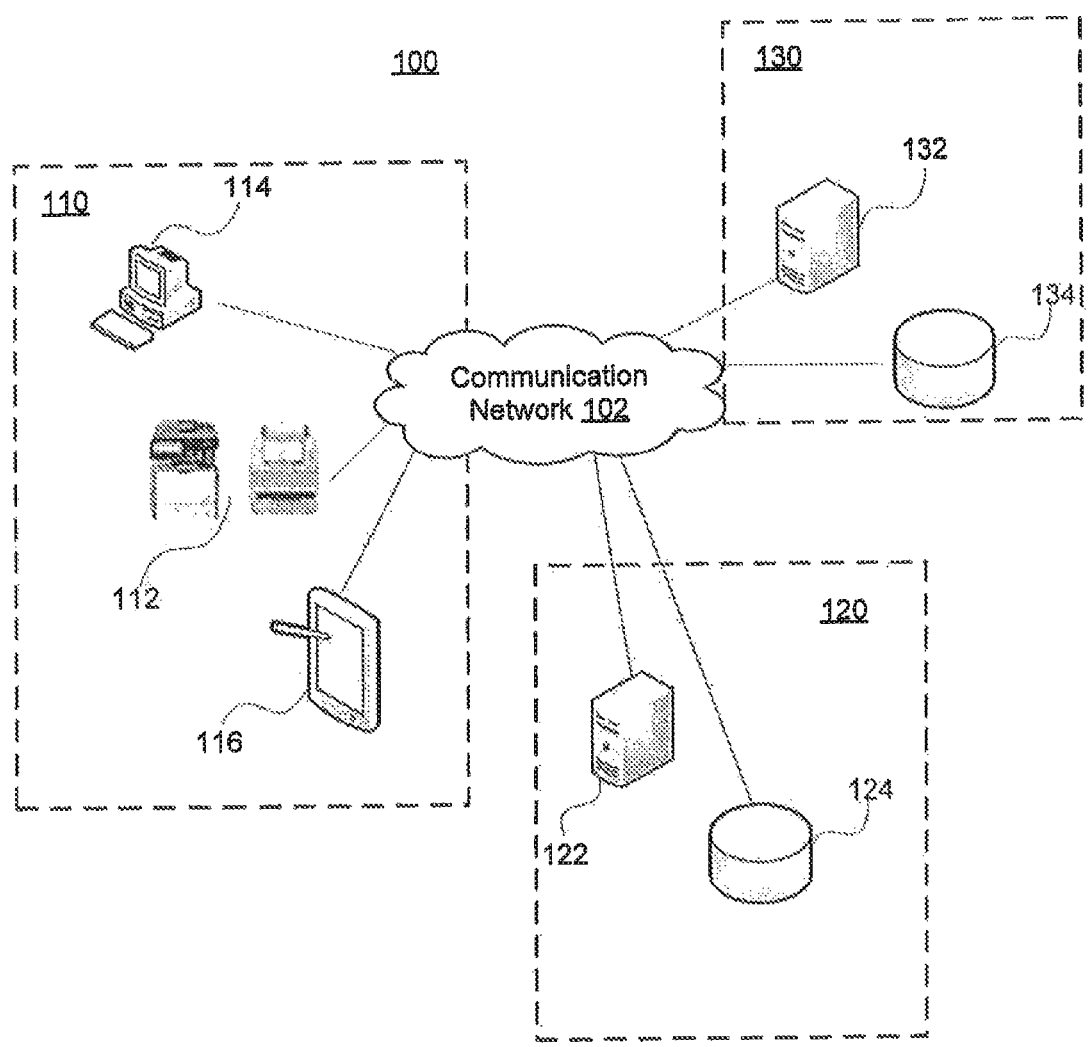
FIG. 1 illustrates an exemplary data capturing and exchange operating environment.

FIG. 1 illustrates an exemplary operating environment 100 that may include a healthcare sub-network 110, a healthcare network server 120, a health information exchange ("HIE") 130, and a communication network 102.

A healthcare sub-network refers to a virtual or physical network containing devices used in healthcare facilities for capturing unstructured data and participating in a structured data exchange with other HIEs via a healthcare network server. A healthcare facility may include an appropriate healthcare organization, such as a hospital, a clinic, a laboratory, or a medical center.

In this description, structured data refers to data in a format recognizable by a recipient or application in a HIE. For example, structured data may include formatted data recognizable by a clinic in HIE 130. The structured data generally includes metadata in addition to ordinary data. On the other hand, unstructured data is not readily recognizable by desired recipients or applications in a HIE.

The devices in healthcare sub-network 110 may include any appropriate data-capturing, -processing, or -management devices, such as a computer, a digital camera, a network scanner, a printer, a fax server, a medical device, a smart phone, or any device having computing functionalities. The devices in the healthcare sub-network 110 may also be off-the-shelf multi-function devices running particular software programs for performing the data-management processes disclosed, or may be customized or customizable multi-function devices capable of performing the data management functionalities disclosed.

For example, healthcare sub-network 110 may include a multi-function device 112 such as multi-function printers, multi-function fax machines, or multi-function scanners, workstation 114, or computer 116. The devices in healthcare sub-network 110 should be capable of capturing, importing, or processing data, especially in unstructured data formats.

The devices in the healthcare sub-network 110 should be connected through one or more internal networks (not shown) or through communication network 102 such that those devices can access services that healthcare network server 120 provides.

Healthcare network server 120 may include appropriate computer servers, software, and databases, in a stand-alone configuration, a cluster configuration, a network configuration, or a cloud computing configuration. These servers should provide enterprise- and server-side services for processing and managing healthcare data. For example, healthcare network server 120 may include a computer server 122 with programs to communicate and exchange data with healthcare sub-network 110 to complete various healthcare data-management processes.

Healthcare network server 120 may also include a storage server 124 to provide database services and database management services. Storage server 124 may store any appropriate data in a central location or in a distributed storage system. Healthcare network server 120 may also communicate with other external systems (e.g., HIE 130) to exchange electronic medical records (EMR) or electronic healthcare records (EHR) using accepted data formats.

HIE 130 may include any appropriate computer servers, software, and databases, also in a stand-alone configuration, a cluster configuration, a network configuration, and/or a cloud computing configuration, and provides various enterprise and server-side services for facilitating, processing, and managing healthcare data. For example, HIE 130 may include a computer server 132 and a database server 134. Computer server 132 and database server 134 may include any appropriate system in a healthcare facility and other locations capable of receiving and processing healthcare information based on a set of standard or known protocols used by healthcare professionals.

Although FIG. 1 only shows one HIE, HIE 130 may include several different HIEs. Further, the HIEs may form an HIE network.

Communication network 102 may include an appropriate network for exchanging data among various devices and computer systems. For example, communication network 102 may be a telecommunication network, a wireless network, or a private and public computer network, including the Internet.

A HIE refers to various types of healthcare systems and networks that allow for the exchange, and in some cases centralized storage, of patient clinical information for throughout a community. Communicating and receiving information on a HIE network may require structured data and defined methods. That is, data that can be shared with systems in the HIE may be required to conform to certain specifications.

Not all data conform to the specifications required for exchanging information on HIE networks. In fact, large amounts of clinical information cannot be shared in the HIE network because either the source or the content created by the source do not conform to certain specifications or protocols, i.e., is not structured, and cannot participate in information exchange.

For example, user computer 116 in the healthcare sub-network 110 may provide unstructured clinical information. As a result, user computer 116 may be unable to participate in the HIE on its own. However, by using services provided by healthcare network server 120, it may become a part of sub-network 110 of unstructured devices to participate in and act as an endpoint for HIEs. In doing so, user computer 116 may utilize a certain set of web services, a middleware layer, and/or other types of services made available by the healthcare network server 120.

Using these services, user computer 116 can collect unstructured data, transform them into structured data, and upload them for further processing such that the data can be shared immediately with different networks. The transformation may also be performed by the server 120. In one embodiment, this process requires little or no user input and greatly simplifies and encourages the input, storage, and exchange of information. That is, using the computer 116 and the services provided in environment 100, a user needs to perform only a single step to image, structure, save, file, and transfer information. This solves many problems arising from prior art healthcare environments.

For example, in many prior art healthcare environments, a patient's complete medical file includes both unstructured documents (e.g., paper, image) and structured electronic files, such as those in an EMR. However, until all unstructured documents are manually entered and filed into the patient's electronic medical file, the patient's medical information in the EMR, as it is available to those not in possession of the unstructured documents, is incomplete. Although many health organizations and networks are going "paperless," few, if any, have and will entirely eliminate unstructured documents. Environment 100 described in FIG. 1 makes it possible to manage the unstructured documents by building the process of handling unstructured documents into existing automated workflows in any healthcare environment.

In one embodiment, the structuring of data needs only be done once through any one of the devices in healthcare sub-network 110, and the structure data is immediately available to all components connected to the communications network 102. Accordingly, this automation of the data input, storage, and exchange greatly reduces the likelihood of human error in handling patient data. Because a document is permanently structured the first time it is imaged by a device and no further data entry, processing, or structuring is needed by other users or networks, the system of environment 100 also minimizes the duplication of labor. All users and components connected to the network 102 may obtain immediate access to a structured and usable patient file.

Another embodiment consistent with environment 100 of FIG. 1 may simplify the procedures for structuring documents within a healthcare network and minimizes delays in information becoming available to others. For instance, a nurse entering information about a patient directly into the EMR may nevertheless fill out a paper form not in the EMR, either for compliancy or convenience reasons. This paper form completed by the nurse then becomes a "floating" document with no designated place for storage until it is handed to a unit clerk, who either scans or mails the document, usually on a periodic basis along with other "floating" documents, to the medical records department for filing. The medical records department, in turn, scans the floating document and may manually enter information from the document into the patient chart. Hours or days may pass until the floating document is added to the EMR and available for retrieval. In the meantime, the nurse, who likely retained a copy of the floating document, may have added or modified information on the floating document, compromising the integrity of the copy of the floating document in the EMR. A nurse using a device in environment 100, on the other hand, may promptly structure and file the floating document in the EMR and directly modify the floating document in the EMR.

Figure 2:
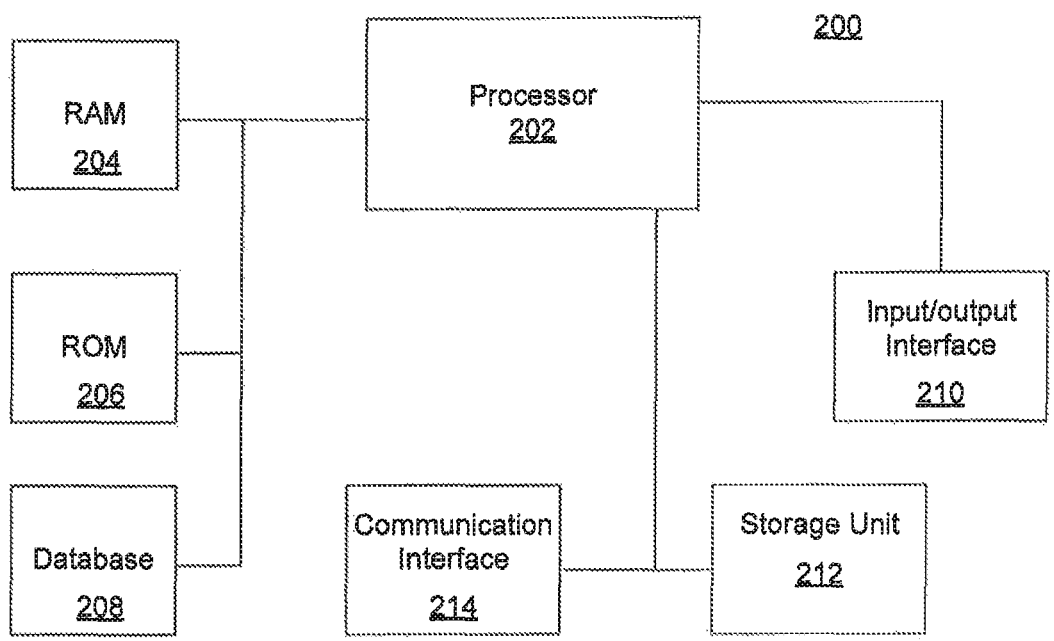
FIG. 2 illustrates a block diagram of an exemplary computing system consistent with the invention.

The various devices and computers (e.g., multi-function devices 112, workstation 114, user computer 116, computer server 122, and computer server 132) in environment 100 may be implemented using any appropriate computing systems and other peripheral or external devices. FIG. 2 shows a block diagram of an exemplary computing system 200.

As shown in FIG. 2, computing system 200 may include a processor 202, a random access memory (RAM) unit 204, a read-only memory (ROM) unit 206, a database 208, an input/output interface unit 210, a storage unit 212, and a communication interface 214. Other components may be added and certain devices may be removed without departing from the principles of the disclosed embodiments.

Processor 202 may include any appropriate type of graphic processing unit (GPU), general-purpose microprocessor, digital signal processor (DSP) or microcontroller, and application specific integrated circuit (ASIC), etc. Processor 202 may execute sequences of computer program instructions to perform various processes associated with computing system 200. The computer program instructions may be loaded into RAM 204 for execution by processor 202 from read-only memory 206.

Database 208 may include any appropriate commercial or customized database for computing system 200, and may also include query tools and other management software for managing database 208. Further, input/output interface 210 may be provided for a user or users to input information into computing system 200 or for the user or users to receive information from computing system 200. For example, input/output interface 210 may include any appropriate input device, such as a remote control, a keyboard, a mouse, a microphone, a video camera or web-cam, an electronic tablet, voice communication devices, or any other optical or wireless input devices. Input/output interface 210 may include any appropriate output device, such as a display, a speaker, or any other output devices. Further, input/output interface 210 may include any external device, such as a scanner, a camera, a fax, or a printer, etc.

Storage unit 212 may include any appropriate storage device to store information used by computing system 200, such as a hard disk, a flash disk, an optical disk, a CR-ROM drive, a DVD or other type of mass storage media, or network storage. Further, communication interface 214 may provide communication connections such that computing system 200 may be accessed remotely and/or communicate with other systems through computer networks or other communication networks via various communication protocols, such as TCP/IP, hyper text transfer protocol (HTTP), etc.

Returning to FIG. 1, during operation, devices in the healthcare sub-network 110 may provide certain electronic healthcare records to recipients in HIE 130. As used herein, electronic healthcare records or electronic medical records (EMR) may refer to any appropriate data, in electronic form, about a person's medical and healthcare status, activities, and history, etc. For example, the electronic medical records may include medical history (e.g., surgical history, medications, family history, social history, habits, immunization history, and development history), medical encounters (e.g., illness and treatment, physical examination, assessment and plan), orders and prescriptions, progress notes, test results, and other attached files and documents, such as digital images, consent forms, EKG tracings, and admission forms. A document may be in any form and may include any content, including but not limited to healthcare related information.

The data provided by the devices in the healthcares sub-network 110 may need to be further processed or shared with HIE 130 over communication network 102. This may be achieved either directly on the devices or facilitated by healthcare network server 120.

For example, the devices may provide healthcare data by scanning various medical records into electronic form, such as scanned files formats in WORD, PDF, JPG, GIF, and TIFF, etc., which are unstructured with respect to the health care exchanges. Further, the devices may transmit the electronic data records in protocols inherent to the devices.

Such electronic data records may be unrecognizable by HIE 130. Services provided by healthcare network server 120 may include services that facilitate, enable, and/or manage the conversion, transfer, and exchange of unstructured healthcare data and/or structured healthcare data such that the data can be recognized and shared by HIE 130. The healthcare network server 120 may also provide necessary services that allow devices 302 to comply with security protocols of the HIE in order to be recognized endpoints on the HIE.

Figure 3:
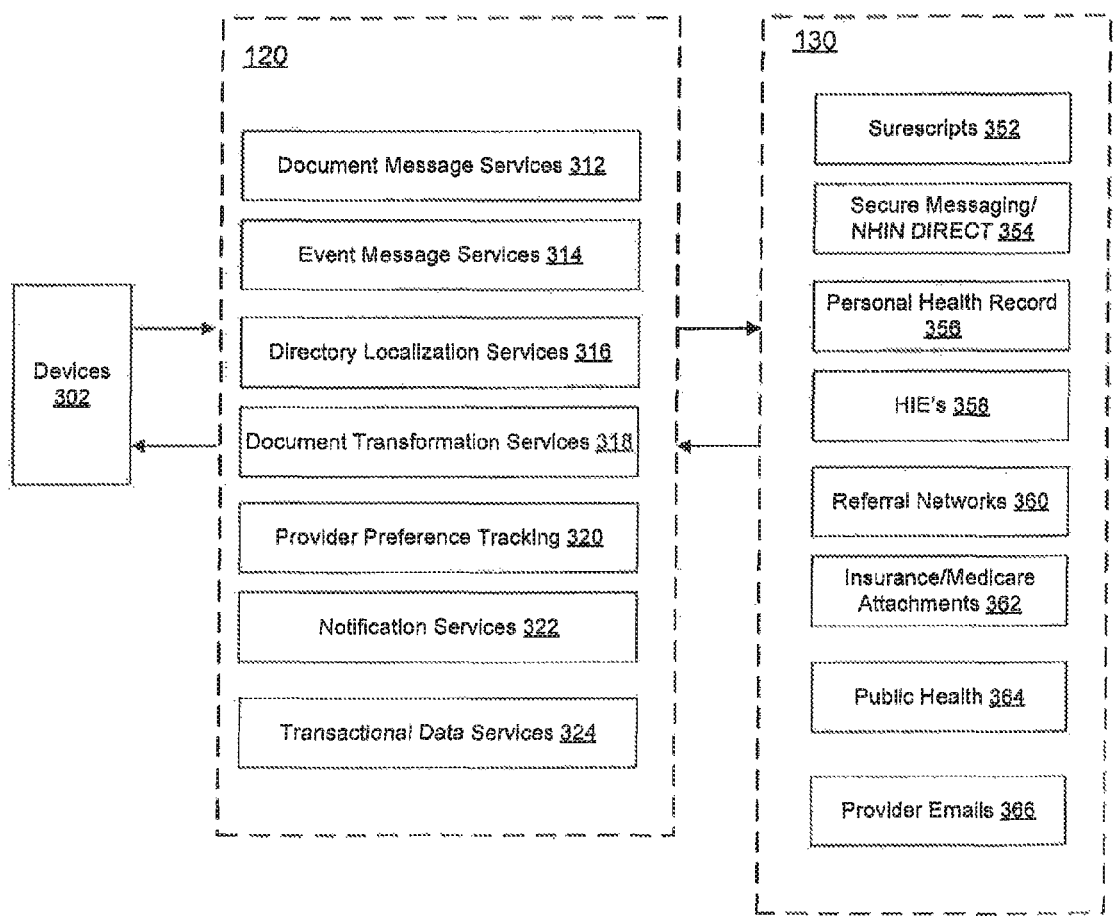
FIG. 3 illustrates an exemplary arrangement of services and entities in the data capturing and exchange operating environment, consistent with the invention.

FIG. 3 shows exemplary services in the healthcare network server 120 and exemplary entities in the HIE 130. The services in the healthcare network server 120 may be provided to devices 302 for processing and managing unstructured data. Devices 302 may include devices in sub-network 110, as well as devices in other sub-networks. For example, the healthcare network server 102 may provide document message services 312, event message services 314, provider directory localization services 316, document transformation services 318, provider preference tracking 320, notification services 322, and transactional data services 324. Certain services may be omitted and other services may be added.

Certain services provided by the healthcare network server 120 may exchange control and data information with the HIE 130 such that the HIE 130 can receive structured data corresponding to unstructured data provided by the devices 302. This exchange of information between the HIE 130 and the healthcare network server 120 may be achieved through various formats, and by various entities/users in the HIE 130. For example, the exchange of information may include surescripts data 352 (e.g., proprietary or DIRECT open network), secure messaging/NHIN DIRECT data 354, personal health record 356, HIE's 358 (e.g., repository, federated), referral network data 360, insurance/Medicare attachments 362, public health data 364, or healthcare provider emails 366.

Users may first obtain or capture unstructured data using one of the devices 302. A device 302 may then request services from the healthcare network server 120 to process the unstructured data such that the corresponding structured data can be automatically generated and sent to the HIE 130. Some processes are described in connection with FIGS. 4-7.

Figure 4:
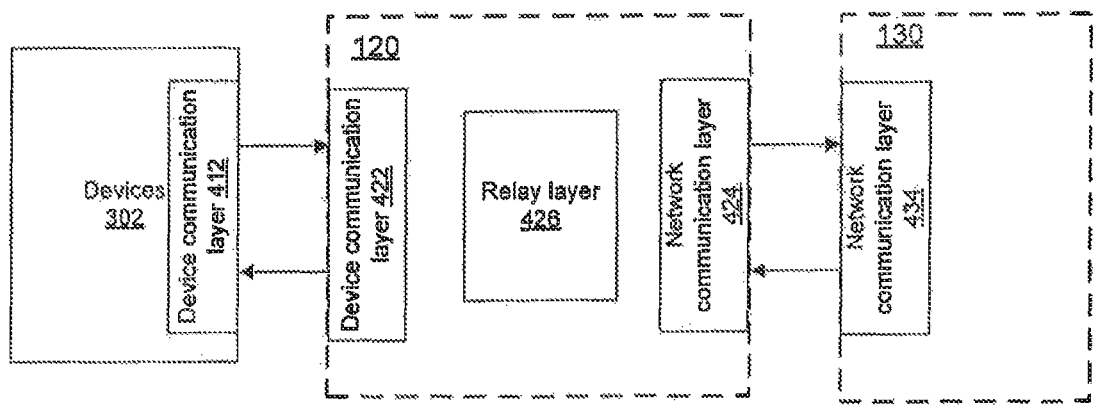
FIG. 4 illustrates an exemplary configuration of data capturing and exchange functionalities and services.

FIG. 4 shows a configuration of data-capturing and exchange functionalities, services, or applications for devices 302, the healthcare network server 120, and the HIE 130 (e.g., computer systems of the HIE 130) that facilitate the exchange of data between devices 302 and HIE 130. These data-capturing and exchange functionalities, services, and applications may be implemented in web services or middleware software programs, etc.

As shown in FIG. 4, a device 302 in the healthcare sub-network 110 may include a device communication layer 412, which may be implemented as a software application running on a healthcare sub-network device or as hardware in device 302. The software application may be provided by the server or by the device manufacturer. The device communication layer 412 of the healthcare sub-network device may communicate with the device communication layer 422 of the healthcare network server 120 such that the various services of the healthcare network server 120, as well as other management and processing functionalities of the healthcare network server 120, may be accessed by the device.

The data exchanged between the device communication layer 412 and the device communication layer 422 may include unstructured data, metadata, and other information such as device security certificates and transactional details. Using this information, the healthcare network server 120 can relay and reformat the unstructured data according to the particular HIE type. For example, device communication layer 412 can provide a standardized set of API calls that allow manufacturers or vendors of document-capture sources to connect to one or more HIEs in a community, eliminating the need for a manufacturer or vendor to customize each document capture source to a particular exchange type. Healthcare network server 120 may include a network communication layer 424 configured to communicate with network communication layer 434 of HIE network based on certain standard or pre-determined protocols or data formats, such that healthcare data can be exchanged between the healthcare network server 120 and the HIE 130. The data exchanged between the network communication layer 424 and the network communication layer 434 may include structured data and other messages.

Network communication layer 434 of the healthcare network server 120 can exchange information with various networks, such as HIEs, insurance exchanges, secure messaging networks, file transfer networks, direct networks (e.g., NHIN direct), repositories (e.g., XDS.b, PHRs, EMRs), public health exchanges, and other P2P health information networks.

Healthcare network server 120 may also include a relay layer 426 for performing data conversion or transformation between unstructured data and structured data, and between formats that are acceptable or required by the specific devices. The relay layer 426 may also perform other control functions, such as access control, security, and automatic determination of recipients of structured data.

Storage server 124 may contain unstructured data. Healthcare network server 120 may monitor and collect statistics on the unstructured data in storage server 124 without structuring the data. For example, server 120 may collect information on the flow of unstructured data, where the unstructured data was created, the size, dates, types of the data, additional steps needed to structure the data, and estimated times to structure the data. Server 120 may then use this information to schedule or recommend schedules for structuring data.

Figure 5:
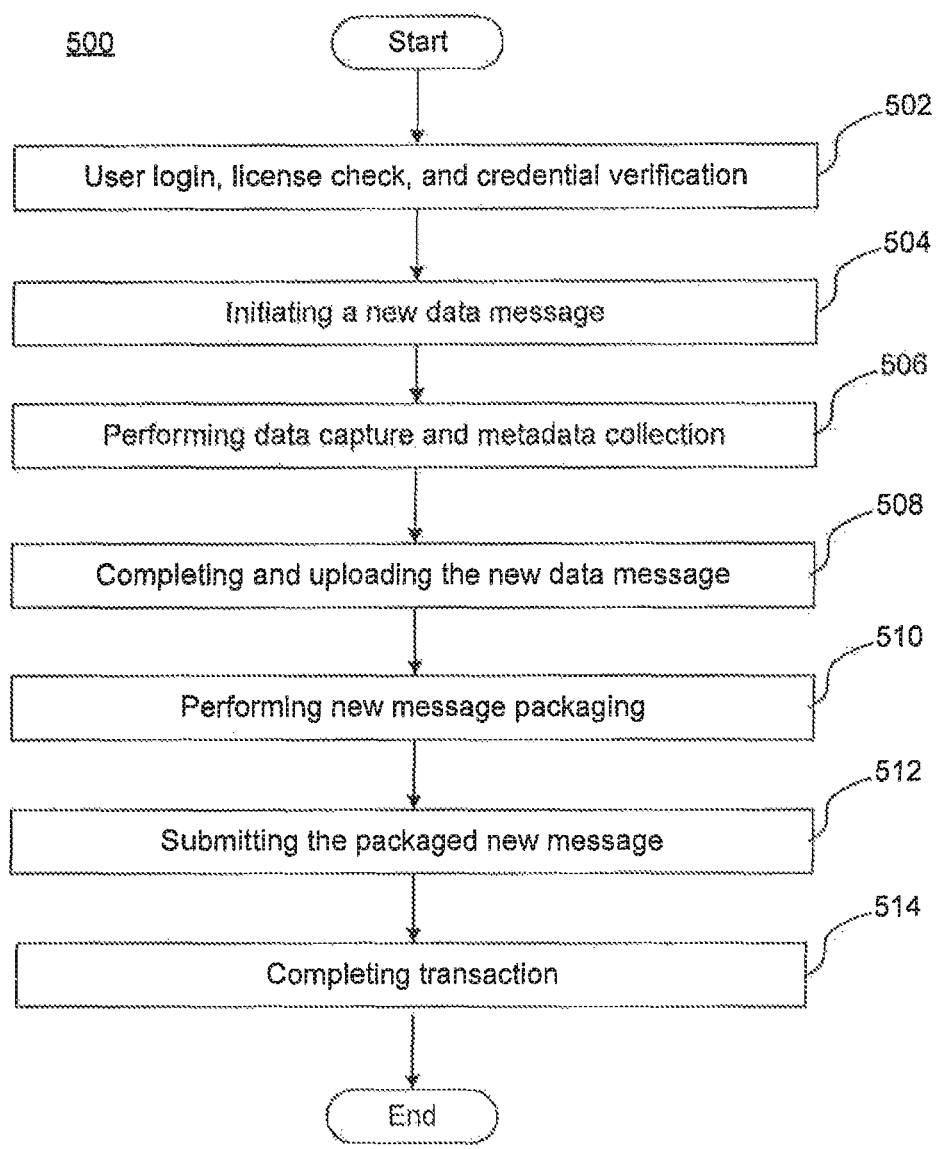
FIG. 5 illustrates an exemplary data capturing and outbound delivery process.

FIG. 5 shows an exemplary data capturing and outbound delivery process 500 performed across device 302, healthcare network server 120, and HIE 130. At the beginning of process 500, a user may log in device 302 to send a data message, such as a document or medical record (502). A data message may also be referred to as a document message, i.e., a message for transmitting a document, and may include a message portion and one or more attached documents. The data message may also include, documents and their associated metadata, with no message portion.

For example, a user who wishes to send a medical record to a doctors office on the HIE network may begin the process by logging in a multi-function device (i.e., device 302) and providing a user name, password, or other similar information. Device 302 may then send the user information to a license server (not shown) in the healthcare network server 120. The license server may include internet-based licensing and data collection tools for multi-function device applications, network scanners, and other unstructured document capture sources (digital cameras, smart phones, medical devices, etc.). The license server may grant a license to the user or the device and administer licensing transactions to allow devices and users to participate in information exchange with, for example, HIE 130. The license server can enable the automatic tracking, installation, and licensing of application software on devices, and collect customer and transactional data to enhance data collection and document capture solutions.

Server 120 may also verify user or device credentials (e.g., certificates) to authenticate the user or device. Further, healthcare network server 120 may store the user's authentication information for automatic verification and connection to the sub-network 110/healthcare network server 120.

After authenticating the user or device and checking for an appropriate license, the user or device 302 may initiate a new data message 504. Device 302 may use the document message services 312 provided by healthcare network server 120 to compose and transmit the new data message.

For example, device 302 may provide an interface for the user to create a new data message, or may allow the user to select an appropriate recipient for the new message. A healthcare provider may be selected from a device address book containing providers' secure addresses, HIE addresses, or endpoint repositories. The device 302 may also obtain provider information from healthcare network server 120 through a directory service to access a provider directory. For example, healthcare network server 120 may use directory localization services 316 to maintain a local directory of service providers on device 302 and to provide query services for device 302 if the device 302 cannot locate a desired recipient using its local directory. If the recipient for the new message is a clinic or similar health group on a HIE, device 302 may require the user to confirm that the patient has consented to the submission of data to the HIE prior to sending the message.

Different HIEs may require different forms and types of consent, and such requirements may be pushed to device 302 through a set of business rules, systems rules, and/or protocols. Server 120 can manage the unique requirements for each type of network and provide web services the device requests with business and system rules in a format that translates to a device the functions that would take place on a device. For instance, different types of networks may require different levels of patient consent before authorizing information exchange. One type of consent level might require a user submitting an unstructured document to indicate, on the device, whether consent is given by the patient. A more advanced network might require a different type of consent, requiring additional information from the patient. In either case, the device may receive the rules for consent from healthcare network server 120 and present those rules to the user through the device software interface. Depending on the business rules, device 302 may provide different interfaces for the user in processing the message. Such consent may have to be obtained from the user through an interface of the device 302 before the information can be sent.

Device 302 may also provide an interface for the user to select multiple destinations simultaneously. For example, if device 302 is a scanner, the user may be able to scan or import a document and select any or all destinations including a directory, an EMR database, a HIE, and a local printer.

Optionally, healthcare network server 120 may collect statistics from devices 302 to enhance performance. Server 120 may also send notifications or advertisements directly to the devices 302, which can be displayed directly on the network component itself. If automatic billing is authorized, server 120 may perform automatic billing and send billing related messages to the devices 302.

Device 302 may perform data capture and metadata collection (506). For example, device 302 may create any appropriate electronic document and collect metadata associated with the electronic document.

To streamline the document capture process in a hospital or large healthcare environment, device 302 (with interface software to healthcare network server 120) may provide users with different views (e.g., options) for data capture on the device 302). In one embodiment, instead of requesting information on the document that the user is scanning, device 302 may automatically push anticipated data to the user based on various environmental factors.

In one embodiment, healthcare network server 120 continuously monitors, collects, and processes information exchanged between components (such as devices 302) connected to the server as well as real-time activities of all components connected to the server. Server 120 may also dynamically update information based on this information, including message-based metadata updating, and push the updated information to components that may use this information, such as devices 302.

Information exchanged between components within the sub-network 110 includes metadata (i.e., data that describes or defines other data) and messages that may be exchanged over a specific messaging network (e.g., part of sub-network 110) such that applications and components can interactively process various types of data based on information exchanged over the messaging network. The physical medium for the messaging network may include any appropriate medium type, such as wireless network, cellular network, local LAN, or other wired or wireless network.

In one embodiment, devices 302 may perform predictive document capture. When predictive document capture is enabled, device 302 may select one or more data capture modes or data capture views to automate and improve the data capture speed. For example, a user logging into device 302 to scan a document may be automatically presented with a list of patients predicted to be the patients who the user will likely associate the document with. The prediction of likely patients by device 302 or server 120 may be based on a number of factors, including patient traffic and activity in the healthcare facility, the location of the device, time of day, the user's identity and actions upon login, the user's history of login and actions upon login, the configuration of the devices and servers, the default views established on the devices, metadata, and relevant information from an EMR, storage medium, and other networks.

The various data capture views may include a registration view, an order view, a proximity view, a schedule view, a schedule view, an activity view, a query view, and a batch scan view, etc.

Using the registration view, device 302 may show all the patients that have been registered within a defined period of time, for example, the last five minutes. For example, a user can walk up to device 302, log in, and see all patient registrations that occurred within a predetermined period of time. Device 302 may search all patients registered within a predetermined period to determine a list of likely patients, and select a particular patient for electronic medical data retrieval. A user or administrator may provide the predetermined period, and the user or device may select particular patient.

Using the order view, device 302 may show orders placed within a defined period of time (for example, last thirty minutes). Device 302 may search the patients having medical records associated with a particular order to determine a particular patient for the electronic medical data. The user may also enter the original laboratory order information to determine the particular patient to associate a captured laboratory result.

Using the proximity view, device 302 may show patients within a certain distance from the device, for example, all patients on the east wing of the 3rd floor. Device 302 may search all patients within a predetermined distance from the device to determine a list of patients fitting the proximity criteria and to determine a particular patient for the electronic medical data. The distance may be entered by the user or an administrator and the particular patient may also be selected by the user.

Using the schedule view, device 302 may show patients scheduled to be seen on a particular date. Device 302 may search all patients associated a particular schedule to determine a list of patients and to further determine a particular patient for the electronic medical data. The schedule (e.g., a date, a time period, etc.) may be inputted by the user or an administrator and the particular patient may also be selected by the user.

Using the activity view, device 302 may show all patients seen in an area (i.e., emergency room) in a certain period, such as the last 8 hours). Device 302 may search all patients seen in an area in a period to determine a list of patients and to further determine a particular patient for the electronic medical data. The area and time period may be inputted by the user or an administrator and the particular patient may also be selected by the user.

Using the query view, device 302 may allow the user to query for a patient record by name, date of birth, ID, etc. Device 302 may search all patients based on the search criteria to determine a list of patients fitting the search criteria and to further determine a particular patient for the electronic medical data. The search criteria may be entered by the user. For instance, the user may enter a last name as search criterion.

Using the batch scan view, device 302 may allow a user to scan documents in a batch without breaks between documents. Device 302 may then collect basic batch data and store the information for further processing.

Additional views are acceptable as well. For example, device 302 may provide a view based on currently open patent records, such as one that the user is already working on. This view may also be based on contextual integration technologies such as CCOW.

The user/device 302 may use one data capture view or a combination of multiple data capture views to capture unstructured data. As discussed above, the appropriate data capture view or views provided to the user may be determined based on metadata. The metadata may be obtained using multiple resources include, for example, the login information of the user, information extracted directly from the document (e.g., text), the message accompanying the document (e.g., time of receipt, sender information, subject and body fields), EMRs, server 120, and information from outside networks through communication network 102. Additionally, metadata may be obtained from the device 302 itself, such as its location, status, serial number, and time of use.

In one embodiment, device 302 may monitor HL7 messages and extract relevant data elements from received messages to be used as metadata. The HL7 messages, as used herein, may refer to any appropriate messages used in HL7 messaging, which are used for communication and data integration between applications and systems within a healthcare facility or facilities. Table 1 illustrates exemplary HL7 messages for obtaining metadata by device 302.

Rather than uploading the message to server 120, device 302 may upload the message to the sub-network 110. The healthcare network server 120 may monitor sub-network 110 and retrieve any new messages from device 302 either immediately upon detection or at predetermined times. For example, healthcare network server 120 may retrieve the new message from device 302 as it becomes available, retrieve the new message along with all new messages from device 302 at a predetermined time, or retrieve the new message along with all new messages from sub-network 110 at a predetermined time. Device 302 may also upload the new message to both sub-network 110 and healthcare network server 120.

TABLE 1

Using HL7 Messages and Metadata

| Message Type | Message Event | Description |
| --- | --- | --- |
| NEW ADMISSION/VISIT ADT—Admission/ Discharge/Transfer SIU—Schedule | A01—New Admit A04—New Registration A05—Pre Admit | Indicates that a patient has been admitted or registered |
| DISCHARGE/CANCEL an ADMISSION/VISIT ADT—Admission/ Discharge/Transfer SIU—Schedule | A03—Discharge A11—Cancel Admit A13—Cancel a discharge | Indicates that a patient has left the hospital or clinic or the appointment has been cancelled |
| PATIENT LOCATION ADT—Admission/ Discharge/Transfer | A02—Transfer A12—Cancel Transfer A17—Bed Swap | Indicates that a patient has been transferred (or cancel a transfer) to another room or location |
| UPDATE PATIENT DETAIL ADT—Admission/ Discharge/Transfer | A08—Update pt. info A31—Update person info A18—merge Pt. records A35—change pt. Account number A36—Change MRN | Update the patient record information (metadata) |
| ORMs Orders OBX ORU - Results | New Order Canceled Order Deleted Order Recurring Order Completed Order | Update the order information for a patient record |

Table 1 shows that certain metadata, such as information about new admission/visit, discharge/cancel an admission/visit, patient location, update patient detail, ORMs orders and other results, may be automatically obtained from HU messaging and used as metadata for data capturing and structuring.

After capturing data, device 302 may include that data in the new data message. Device 302 may also provide an interface for the user to view and edit images or messages on the device.

Device 302 may also provide an interface for a user to perform document and patient breaking. This feature allows a user to insert patient breaks in each new message or document breaks between files attached to the message. This feature may also include alerts after such breaks are inserted or removed, such as an alert to the user that a change will be made to the patient data associated with the new message.

After the data capture and metadata collection process (506), device 302 may complete the message with the data and, if desired, the metadata, and upload the message to healthcare network server 120 (508). A user or an administrator may automate this process by allowing device 302 to generate a standard message body and automatically upload the message without requiring further user input. Device 302 may also provide a standard message body and allow user edits or confirmation before uploading the message. Thus, the uploading the message to the healthcare network server 120 may be automatic or may occur upon user confirmation and input, such as the selection of a "send" command or button.

After server 120 obtains the new message from device 302 or sub-network 110, server 120 may perform further processing on the new message. For example, healthcare network server 120 (e.g., using relay layer 426) may perform new message packing (510). New message packaging includes the use of document transformation services 318 to package a new data message as a packed data message in one or more formats. New message packing is explained in further detail below.

Because of the range and variety of information that device 302 may capture, the potential file and data types encountered or required to exchange information with a different HIEs may vary. Healthcare network server 120 allows the device 302 to handle potential incompatibilities with different HIEs by packing the messages, i.e., converting messages from device 302 to one or more formats accepted or required by the desired recipients. This allows the information to be consumable or creatable by an endpoint and the HIE 130. For example, healthcare network server 120 may perform conversions for these current HIE initiatives: XML to/from Image (PDF, GIF, TIF, JPG, BMP, PNG); CDA to/from Image; CDA to/from eDoc (.DOC, .DOCX, .TXT, .RTF); XDS to/from Image; XDS to/from eDOC; HL7 Message to/from Image; and HL7 Message to/from eDoc, etc. Thus, a packed message may take various formats, such as image, eDoc, XML, HL7, CDA, and XDS, etc. Server 120 can also provide a method for identifying document types and the associated codes for a customer's organization and for creating a rule set that allows for the mapping of document types used by other customers (and are equivalent to an internal document type). When a document is received from an external organization, the type may be mapped to a known document type, thus allowing the document to be automatically uploaded to an internal system, such as an EMR.

In packing messages into certain formats, such as CDA/XDS-SD, healthcare network server 120 may obtain additional metadata in order to perform packing properly. For example, server 120 may create standardized XML information with dynamic metadata elements. The dynamic metadata elements may be generated from multiple devices 302 through the submission of an image with a set of core metadata by each device 302 to the healthcare network server 120. Server 120 may then add additional metadata elements to the dynamic metadata elements to create a structured CDA/XDS-SD package.

Additional metadata may include OIDs (object identification) and UUIDs (universally unique identifier), used in numerous healthcare IT protocols including HL7, CDA, XDS, etc. OIDs, for example, are assigned for interoperability and long-term integration at an entity/organization, provider, document, or transaction level. Healthcare network server 120 may provide an interface for inputting and managing OIDS for an organization that allows for consistency through the organization and for document interoperability. In some instances, server 120 may use web services for the assignment and management of OIDs and may retrieve relevant OIDs for use in the construction or packaging of an item such as a CDA document.

The format of the packed message may be based on a recipient's preference. For example, server 120 may perform provider preference tracking 320 to determine preferences of each provider participating in the HIE. These provider preferences include file formats, EMR specification, workflow routing, device routing.

The message packing may be performed locally on device 302 using information from the device, the user, and any data the device retrieved from sub-network 110 or healthcare network server 120. This may be performed according to a user's preference or as a backup when information from server 120 is unavailable.

After message packing (510), healthcare network server 120 may submit the packed new data message to one or more destined HIE 130 (512).

When submitting the packed new data message, server 120 may first validate the recipient of the packed message (e.g., a HIE). For example, healthcare network server 120 may maintain directories available to devices 302 for performing validation. These directories may include separate address books of participants or endpoint repositories by different HIEs. Server 120 may also provide a selection or aggregation of local directories, or certain geography-based repositories for access by either specific devices 302 or all devices 302 within sub-network 110.

When the recipient is an EMR database or other type of patient database or repository, healthcare network server 120 may perform an indexing operation, such as an automated search in the EMR database or other patient databases to reconcile the patient with an existing patient record using, in part, the metadata in the message transporting documents. If no record is found, the user on device 302 may be prompted to look for or create a new patient record. The user may also select and confirm a document type from an internal document type list. Further, healthcare network server 120 may submit or upload the message or documents directly to the EMR database or other patient database.

After healthcare network server 120 validates the recipient of the packed message, it may complete the message transaction (514). Healthcare network server 120 may do so by encrypting the packed message and routing it to the recipient.

Healthcare network server 120 may also handle message acknowledgment receipts from HIE 130. For example, after receiving a message from server 120, the recipient (e.g., EMR database or HIE) may acknowledge the message by sending back an event message. The event message may include status information and other information related to the receipt of the message from server 120. Healthcare network server 120 may also relay the event message to device 302. After acknowledging a message, the outbound message delivery process 500 may be completed.

Figure 6:
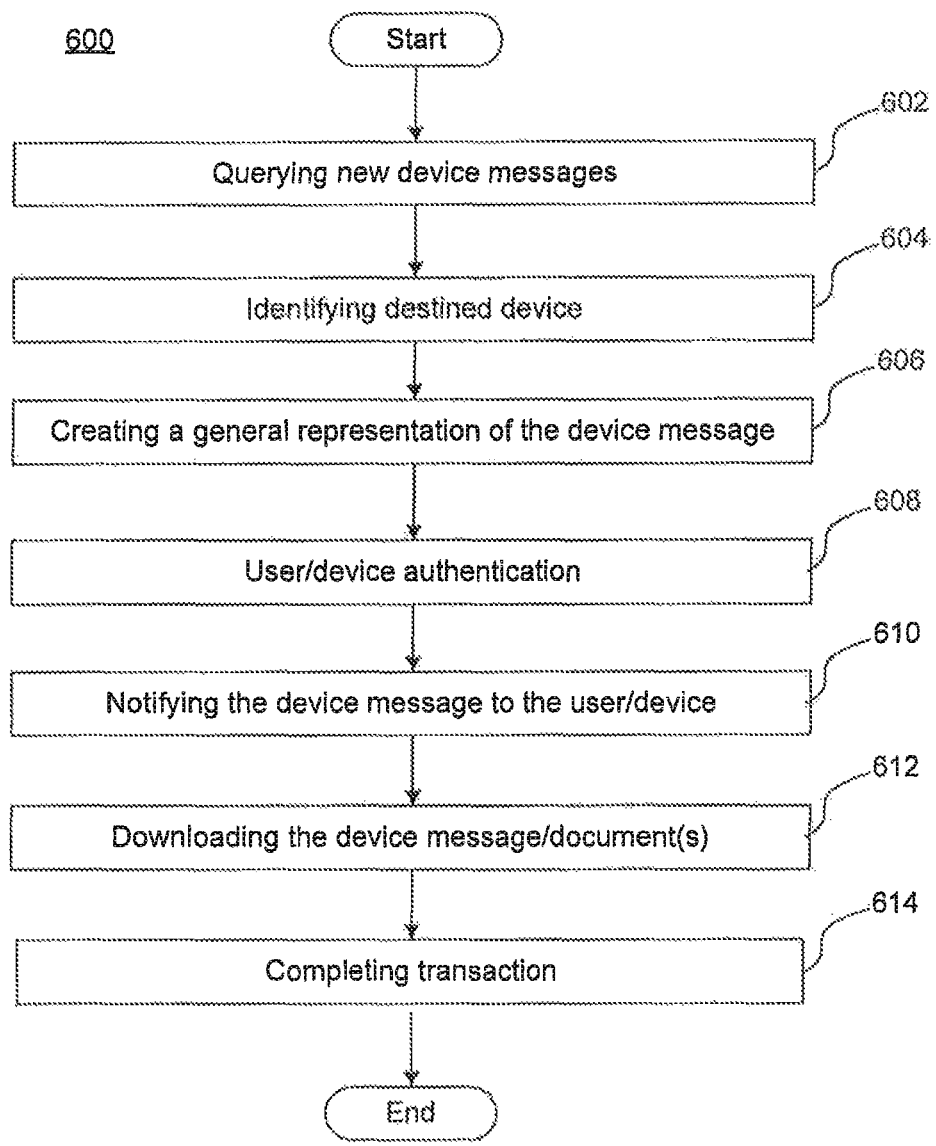
FIG. 6 illustrates an exemplary inbound message delivery process.

FIG. 6 shows an exemplary inbound message-delivery process 600 performed across device 302, healthcare network server 120, and HIE 130, consistent with the disclosed embodiments. Periodically, HIE 130 may receive data messages, such as messages from an entity in HIE 130, destined to certain devices 302. HIE 130 may queue the received data message and wait for healthcare network server 120 to query for such data messages. As shown in FIG. 6, at the beginning of the process 600, the healthcare network server 120 may query a HIE 130 for such new messages for devices 302 or the sub-network 110 (602).

Healthcare network server 120 may periodically query HIE 130. Query messages from healthcare network server 120 may include identifications of server 120, sub-network 110, or devices 302. After receiving a query message from server 120, HIE 130 may validate the message recipients and send the messages destined for devices on the sub-network 110 to healthcare network server 120.

After receiving the data message from HIE 130, healthcare network server 120 may identify a destined device for the data message (604). Healthcare network server 120 may also determine the organization to which device 302 belongs, include this information in the data message, and send an alert about the message receipt to the organization in lieu of or in addition to the device.

Because different devices 302 may each recognize only certain type or types of documents, healthcare network server 120 may generate a general representation of the message or document that can be recognized by all devices 302 (606), and provide this general representation to the device 302. For example, the healthcare network server 120 may create a thumbnail recognizable by all devices 302 for the message or document such that all devices 302 may be able to view the thumbnail.

Healthcare network server 120 may also perform user or device authentication (608) before message delivery. For example, server 120 may perform a license or a user-credential check at receiving device 302.

Server 120 may also alert device 302 to the received message (610) before message delivery. For example, server 120 may use notification service 322 to indicate, in an "inbox" of the user/device 302, that a new message has been received. The healthcare network server 120 may include a preview of the received message for the inbox of the user/device 302. The preview may display a portion of the data message or the attached document, and the user can determine, from the preview, whether to retrieve the entire message or the attached document.

If device 302 decides to retrieve the entire message or document, device 302 may download the message or document from server 120 (612) as well as any associated metadata. Device 302 may further process the message, document, and metadata. This further processing may require a document or message to be converted to a different format. In one embodiment, format conversion may be automatically performed upon the receipt of the message, and prior to any request for document download. In doing the conversion, healthcare network server 120 may first determine the formats supported by the device requesting the document download, and then convert the received message or document into the appropriate format, such as an unstructured data format device 302 can recognize. The details of the format conversion are described above.

Device 302 may perform other processing on the message after it is downloaded from healthcare network server 120. For example, device 302 may further process the message, document, and metadata based on functions and services available to the device, and upload the document into an EMR database, either directly or through healthcare network server 120.

After all necessary and optional processing, device 302 and healthcare network server 120 may complete the inbound message transaction (614). Device 302 may also send a confirmation for the successful receipt of the message or document to healthcare network server 120. The healthcare network server 120 may acknowledge the message receipt by sending an event message to HIE 130 using event message services 314. The event message may indicate status information and other related information on the receipt of the message from HIE 130. HIE 130 may also acknowledge or confirm the success delivery of the inbound message or document to healthcare network server 120.

In addition to being used in outbound and inbound message deliveries, event messages may also be used in other situations among devices 302, healthcare network server 120, and HIE 130. These events may be handled by event message services 314 in server 120. In doing so, an unstructured device 302 on the sub-network which would not otherwise be aware of certain events taking place on, for example, a HIE network, may learn of such events. For instance, healthcare network server 120 (e.g., relay layer 426) may consume and generate events from the HIE network that relate to, for example, the sending and receiving of document messages, endpoint activity, network challenges, recipient or sender compatibilities, etc., and may make appropriate events available to endpoints (e.g., devices 302) for messaging to the end users.

Figure 7:
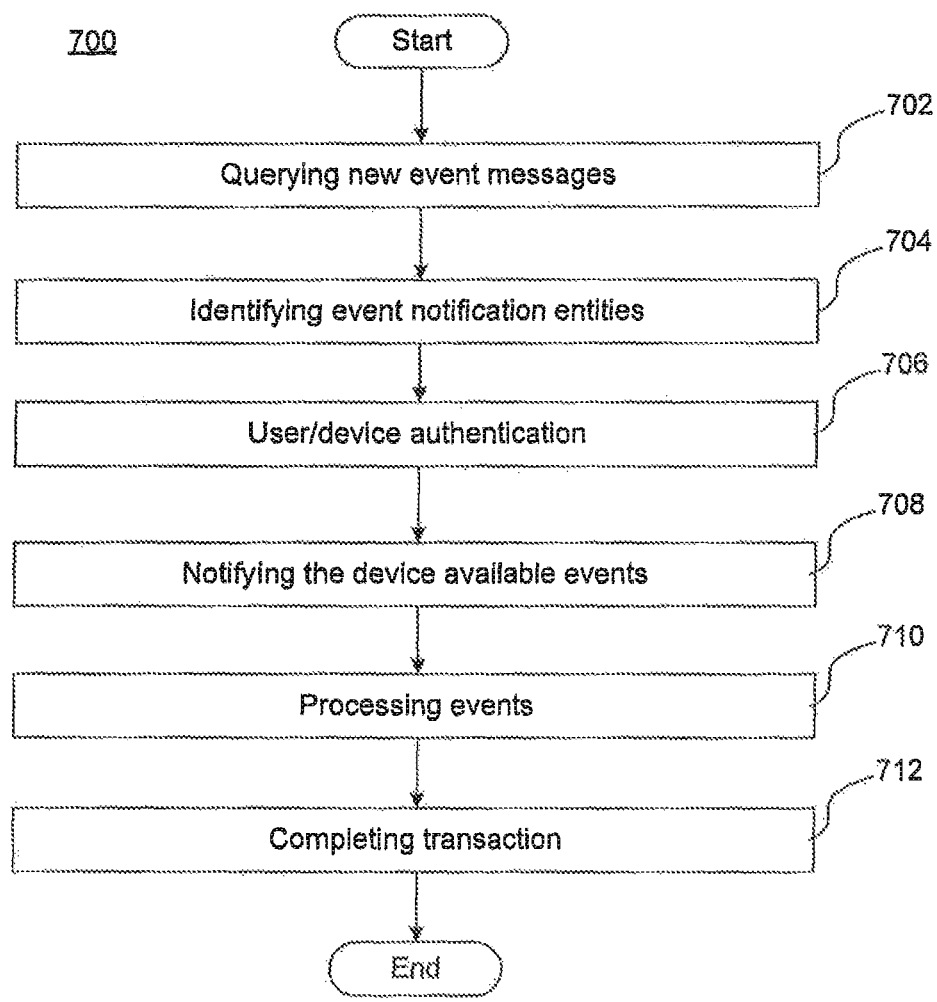
FIG. 7 illustrates an exemplary event handling and notification process.

FIG. 7 shows an exemplary event handling and notification process 700 for event message services 314 performed across device 302, healthcare network server 120, and HIE 130. Periodically, the HIE 130 may receive event messages sent to addresses of healthcare network server 120, devices 302, or sub-network 110. HIE 130 may queue the received event messages and wait for healthcare network server 120 to query for such messages. As shown in FIG. 7, at the beginning of process 700, healthcare network server 120 may query HIE 130 for such new event messages for healthcare network server 120, devices 302, or sub-network 110 (702).

Server 120 may query HIE 130 periodically. An event query message from the healthcare network server 120 may include certain identifications of server 120, sub-network 110, or devices 302. After receiving the event query message from the healthcare network server 120, HIE 130 may send all available event messages destined for server 120, devices 302, or sub-network 110 to server 120.

After receiving the new event messages (702), server 120 may identify event notification entities (704). For example, server 120 may use notification services 322 to filter new events to select destinations (e.g., organizations, devices, etc.) for the events, or the server 120 may choose to send the events to all devices on sub-network 110.

Server 120 may also perform user or device authentication (706), For example, healthcare network server 120 may perform license check or user credential check for the receiving user/device 302.

Further, healthcare network server 120 may notify devices 302 for the available events (708). For example, server 120 may indicate in an "inbox" of user or device 302 that a new event is received for that user or device. Server 120 may also indicate a type, priority, identification, or applicable filters for the new events.

User or device 302 may process the new events (710). For example, the user may review the events on device 302 and perform certain actions. After the event is reviewed or processed by device 302, device 302 may complete the event transaction (712). The transaction completion may include clearing the event on device 302, and sending an event ID cleared on device 302 to server 120. Server 120 may in turn clear the same events on itself.

In addition, healthcare network server 120 may provide other functionalities to maintain, control, and facilitate operation of sub-network 110. For example, healthcare network server 120 may perform transactional data services 324, such as track transactional data surrounding unstructured data and document exchange activity to and from devices 302 on sub-network 110 to various recipients on different HIEs 130. Server 120 may analyze the transactional data to provide additional services or present analytics data to other healthcare applications.

The disclosed systems and methods may provide many advantageous healthcare data management applications. For example, by using the disclosed systems and methods, a sub-network of many and varied devices and sources of unstructured content can participate in HIE. The sub-network can provide device licensing; management; sign up, identity proofing and registration of the devices; on-ramp and off-ramp services that allow the devices and source information to be usable for HIE; broker communications with the devices and networks based upon varied device communication protocols and healthcare IT standards; translation of documents and data to various types applicable to the device, provider, and workflow; and analysis and reporting on unstructured sources, activities, and transaction detail, etc.

Although the systems and methods disclosed are for a healthcare environment, other industries can use these systems and methods for data structuring and management. For example, in legal industry, real property industry, or other financial and business environments, a large amount unstructured legal documents can be efficiently structured by using the disclosed systems and methods. Other applications, improvements, and modifications are obvious to those skilled in the art.

APPENDIX A

Exemplary applications using Inofile ™ and 3$^{rd}$ Party software.

DEVICE APPLICATIONS

The Inofile Relay ™ platform (an exemplary embodiment of Relay Layer 426) allows

APPENDIX A-continued

Exemplary applications using Inofile ™ and 3rd Party software.

for devices to participate on the network. The devices may or may not be installed with Inofile device software.

INSTALLED WITH INOFILE DEVICE SOFTWARE

1. Inofile Device software (Inofile ChartMD ™)
2. Inofile Device software (Inofile Messenger ™)

With the Inofile software loaded on the device, the device is immediately recognized on the network. However, the device/organization/user must still be approved before messages can be sent or received. (See below).

3RD PARTY DEVICE SOFTWARE

Devices by 3rd party hardware or device manufacturers may access Relay by creating an application that uses/communicates with designated Inofile Relay web services. The web services manage the certificate, security, authentication, business rules, provider directory viewing and addition, document metadata and image uploads and network communications. Once included in the 3rd party application, the device can be recognized on the network. With the Inofile software loaded on the device, the device is immediately recognized on the network. However, the device/organization/user must still be approved before messages can be sent or received. (See below)

WEB BASED ACTIVATION, REGISTRATION

A complete registration process must be completed before an organization/user can use the Relay software and also participate on a HIE network. This process is extremely critical when devices and the software are acquired over the web or through an online source, such as an IT service and hardware distributor. However, to allow and enable as many of the organizations in healthcare as possible (despite their size, technology aptitude, etc.) web based acquisition is critical to reaching the markets.

When a device with either the Inofile application or 3rd party device application is purchased and the user activates the software, they follow the process defined below. The process achieves major business objectives for Relay and fulfills business/security requirements for the HIE in identifying and proofing the customer as a valid medical provider and is approved to send patient information over the network. Based upon the type of network and security requirements, the process alters.

PROCESS

NEW DEVICE ACQUIRED
1. User purchases "Relay enabled" device
2. Device is placed at the customers office
   a. User selects the "Relay" button on the front screen of the device
   b. The user is prompted to enter their email to start the registration process
3. User receives email initiating the registration process.
   a. If a user has acquired more than one device, they still initiate via one device and then group the rest of the hardware later in the process through the Web portal.

INITIAL WEB REGISTRATION
4. User clicks on secure link in email and is brought to the Inofile Relay Registration process.
5. User is brought through the following configuration items:
   a. Registration: collection of organizational and contact information
   b. Identity Proofing: requirements for identifying and validating that the customer is able to be a participant on the network.
   c. Billing Configuration: Depending on the hardware and/or distribution, the user is prompted to complete the appropriate billing components
   d. Admin User Account: provide initial user account, customer selects password.
   e. Confirmation Code: User is emailed security code to enter into the initial device. This is used as a first level proofing that the customer is who they say they are and they have the device in their possession.

HARDWARE CONFIRMATION
6. User receives email with a time-sensitive confirmation code
7. User walks back to original devices
8. User selects the Relay button and enters code provided in email
9. Device authenticates with the Relay/Inofile license server and the process of identity proofing the customer is initiated.
   a. Please note - Identity proofing can take minutes up to hours. Relay does not proceed until the user has been approved.
10. Customer receives email stating the identity proofing process has been initiated and will be alerted when the process has been completed.
    a. Behind the scenes, Relay creates an entry into the Surescripts provider directory for the customer and auto assigns a device secure address at the organization level
    b. Behind the scenes, Relay also confirms billing/payment methods CONTINUING REGISTRATION
11. If customer is identity proofed successfully, the customer receives another email requesting they complete the registration and configuration process.
12. The user clicks on the email link provided to bring them to the Inofile Relay Portal
13. The remaining registration process is as follows:
    a. User logs in with the original admin account

APPENDIX A-continued

Exemplary applications using Inofile ™ and 3rd Party software.

b. User completes the following
   i. Security configuration: addition of users that can send and/or receive secure messages
   ii. Address creation: User can create additional secure addresses and assigns the addresses back to the user accounts for use.
   iii. Device Grouping: Customer can add devices (and confirms additional fees) to their account.
       1. If the customer adds one or more devices, they receive an email with another security code that must be entered into each device upon first use after login. This serves as a hardware validation measure that the device is approved and "grouped" back to the customer.
   iv. Document Type configuration: To allow for true interoperability, user configures their OID's and CDA document types for exchange. Document types appear on the device.
   v. Preferences:
       1. File formats
       2. HL7 message configuration engine
       3. Add most favored groups to send to
          a. "notifications sent out alerting trading partners"
   vi. Downloads: Download Inofile Desktop for inbox management
       1. Free version - includes receipt with print only
       2. Activated version - includes stand along capabilities with export to CDA or EMR friendly directory structure
       3. Upgraded version - includes direct integration with major softwares, such as EMR vendors
14. Once the user has completed, the above registration process, the device(s) are now enabled to send message on the Relay network and the organization can receive via Inofile Desktop.

RELAY DESKTOP SOFTWARE

The Relay desktop software integrates with a multi-function device or sending device for sending of new messages and also provides an inbox interface to receiving and processing inbound secure messages. The application allows for very efficient handling of secure messages and attachments and other documents scanned from the device or imported. After downloading the messages/attachments from Relay, the desktop documents/images are processed in the software and uploaded/exported to either an EMR friendly directly structure or directly to the EMR.

In healthcare, many organizations would like to perform a quality check on information before it is submitted to their system (such as an EMR) as the information may overwrite existing information already in the EMR. The Desktop software automates the process of identifying and attaching the documents to the right patient and provider, but allows the user to approve the information (and update if necessary) before submitting directly to the EMR. It provides a single interface and methodology for documents and attachments of all formats, structures (or lack there-of), source, and workflow requirements.

RELAY "PRINT" DRIVER/FILE UPLOAD

Oftentimes in healthcare, documents are stored from an electronic source, such as a clinical system or a billing system. These documents will need to be shared with other organizations. The method for exchange today is to print the documents and fax or print to a fax driver and send.

Inofile Relay provides a "print" driver that can be integrated into software applications such as a clinical system. The print driver provides an API where the clinical software passes the document (scanned image, electronic file, etc.) along with defined metadata to the driver. The driver then prompts the user to select the recipient of the message and confirm the body, subject. Once confirmed, the user hits the SEND button and the recipient address, document and metadata are uploaded to Relay. Relay then structures into a CDA document type, creates the package, encrypts the package and submits over the designated HIE network.

What is claimed is:

1. A method for capturing and transmitting data for a system having a sub-network with devices and a network server connected to the sub-network, comprising:

monitoring the sub-network for pre-determined types of messages;

extracting relevant data elements from the pre-determined types of messages to be used as the metadata;

determining a data capture view based on the metadata;

capturing an unstructured document based on the data capture view to provide information about the unstructured document, the unstructured document being a document that may be in different formats and mediums and is not readily recognizable by applications in the sub-network;

collecting, by one of the one devices, metadata associated with the unstructured document;

sending, by the network server, a packed message containing a structured document in a format that allows a recipient to analyze the unstructured document.

2. The method according to claim 1, wherein the data capture view includes one or more of a registration view, an order view, a proximity view, a schedule view, a schedule view, an activity view, a query view, and a batch scan view.

3. The method according to claim 1, further including:

determining, by the one device, the recipient for the unstructured document in a health information exchange;

composing, by the one device, a data message containing the unstructured document;

obtaining, by the network server, the composed data message; and placing, by the network server, the composed data message into the packed message containing the structured document corresponding to the unstructured document.

4. The method according to claim 3, wherein composing a data message further includes:

inserting breaks into the data message to indicate separate patients or documents.

5. The method according to claim 3, wherein obtaining the composed data message containing the unstructured document further includes:

receiving, by the network server, the composed data message sent from the device.

6. The method according to claim 3, wherein obtaining the composed data message containing the unstructured document further includes:

monitoring the sub-network for data messages;

detecting the composed data message transmitted by the one device into the sub-network; and obtaining the detected composed data message.

7. The method according to claim 3, wherein packing the composed data message into a packed message further includes:

determining a conversion type for the structured document;

obtaining additional metadata corresponding to the conversion type;

converting the unstructured document to the structured document by adding the additional metadata.

8. The method according to claim 3, wherein sending the packed message to the recipient further includes:

validating the recipient using an address book of the health information exchange;

encrypting the packed message; and routing the encrypted message to the recipient in the health information exchange.

9. The method according to claim 1, further including, before capturing the unstructured document:

performing a credential check of the device; and verifying the user credential of the device.

10. A method for capturing and transmitting data for a system having a sub-network with devices and a network server connected to the sub-network, comprising:

capturing, by one of the devices, an unstructured document, the unstructured document being a document that may be in different formats and mediums and is not readily recognizable by applications in the sub-network;

collecting, by the one device, metadata associated with the unstructured document;

determining, by the one device, a recipient for the unstructured document in a health information exchange;

searching a provider directory on the one device to determine the recipient;

querying the network server to determine the recipient for the unstructured document when the recipient cannot be found in the provider directory;

composing, by the one device, a data message containing the unstructured document;

obtaining, by the network server, the composed data message;

placing, by the network server, the composed data message into a packed message containing a structured document corresponding to the unstructured document; and sending, by the network server, the packed message to the recipient in a format that allows the recipient to analyze the document.

11. The method according to claim 10, further including:

determining multiple recipients simultaneously for the unstructured document.

12. A data capturing and exchange system, comprising:

a sub-network having devices, each device being configured to:

monitor the sub-network for pre-determined types of messages, extract relevant data elements from the pre-determined types of messages to use as metadata, determine a data capture views determined based on the metadata collected by the device, capture an unstructured document based on the data capture view to automatically provide information about the unstructured document, the unstructured document being a document that may be in different formats and mediums and is not readily recognizable by applications in a health information exchange, collect metadata associated with the unstructured document, determine a recipient for the unstructured document in a health information exchange, and compose a data message containing the unstructured document; and a network server connected to the sub-network to enable the devices to participate in a health information exchange based on structured data, the network server being configured to:

obtain the composed data message, place the composed data message into a packed message containing a structured document corresponding to the unstructured document, and send the packed message to the recipient in the health information exchange using a format that allows the recipient to recognize and analyze the document.

13. The data capturing and exchange system according to claim 12, wherein the data capture view includes one or more of a registration view, an order view, a proximity view, a schedule view, a schedule view, an activity view, a query view, and a batch scan view.

14. The data capturing and exchange system according to claim 12, wherein the network server is further configured to:

receive the composed data message sent from the device to the network server.

15. The data capturing and exchange system according to claim 12, wherein the network server is further configured to:

determine a conversion type for the structured document;

obtain additional metadata corresponding to the conversion type;

convert the unstructured document to the structured document by adding the additional metadata.

16. The data capturing and exchange system according to claim 12, wherein the network server is further configured to:

validate the recipient using an address book of the health information exchange;

encrypt the packed message; and route the encrypted message to the recipient in the health information exchange.

17. A data capturing and exchange system, comprising:

a sub-network having devices, each device being configured to:

capture an unstructured document, the unstructured document being a document that may be in different formats and mediums and is not readily recognizable by applications in a health information exchange, collect metadata associated with the unstructured document, search a provider directory locally on the device to determine a recipient for the unstructured document, query the network server to determine the recipient for the unstructured document when the recipient cannot be found in the provided directory, compose a data message containing the unstructured document; and a network server connected to the sub-network to enable the devices to participate in a health information exchange based on structured data, the network server being configured to:

obtain the composed data message, place the composed data message into a packed message containing a structured document corresponding to the unstructured document, and send the packed message to the recipients using a format that allow the recipients to recognize and analyze the document.

18. A data capturing and exchange system, comprising:

a sub-network having devices, each device being configured to:

capture an unstructured document, the unstructured document being a document that may be in different formats and mediums and is not readily recognizable by applications in a health information exchange, collect metadata associated with the unstructured document, determine multiple recipients simultaneously for the unstructured document, compose a data message containing the unstructured document; and a network server connected to the sub-network to enable the devices to participate in a health information exchange based on structured data, the network server being configured to:

obtain the composed data message, place the composed data message into a packed message containing a structured document corresponding to the unstructured document, and send the packed message to the recipient in the health information exchange using a format that allows the recipient to recognize and analyze the document.

19. A data capturing and exchange system, comprising:

a sub-network having devices, each device being configured to:

capture an unstructured document, the unstructured document being a document that may be in different formats and mediums and is not readily recognizable by applications in a health information exchange, collect metadata associated with the unstructured document, determine a recipient for the unstructured document in a health information exchange, and compose a data message containing the unstructured document; and a network server connected to the sub-network to enable the devices to participate in a health information exchange based on structured data, the network server being configured to:

obtain the composed data message, place the composed data message into a packed message containing a structured document corresponding to the unstructured document, and send the packed message to the recipient in the health information exchange using a format that allows the recipient to recognize and analyze the document, and wherein one of the devices is further configured to:

insert patient and document breaks into the data message.

20. A data capturing and exchange system, comprising:

a sub-network having devices, each device being configured to:

capture an unstructured document, the unstructured document being a document that may be in different formats and mediums and is not readily recognizable by applications in a health information exchange, collect metadata associated with the unstructured document, determine a recipient for the unstructured document in a health information exchange, and compose a data message containing the unstructured document; and a network server connected to the sub-network to enable the devices to participate in a health information exchange based on structured data, the network server being configured to:

obtain the composed data message, place the composed data message into a packed message containing a structured document corresponding to the unstructured document, and send the packed message to the recipient in the health information exchange using a format that allows the recipient to recognize and analyze the document, and monitor the sub-network for data messages;

detect the composed data message transmitted by the device into the sub-network, and obtain the detected composed data message.

21. A method for a capturing and transmitting data in a system having devices in a sub-network and a network server connected to the sub-network, comprising:

querying, by the network server with a health information exchange, about any data message destined to the sub-network;

receiving, by the network server, a data message containing a structured document and destined to the sub-network;

identifying, by the network server, a device in the sub-network for receiving the data message;

creating, by the network server, a general representation of the data message;

indicating the message, by the network server on an inbox of the device of the data messaging based on the general representation;

receiving, by the device, an unstructured document corresponding to the data message; and acknowledging, by the device, receipt of the unstructured document to the network server.

22. The method according to claim 21, further including:

converting, by the network server, the structured data from the health information exchange to the unstructured data readable by the device.

23. The method according to claim 21, before indicating on an inbox of the device, further including:

performing a credential check of the device; and verifying a user credential of the device.

* * * * *

UNITED STATES PATENT AND TRADEMARK OFFICE
CERTIFICATE OF CORRECTION

PATENT NO. : 9,106,713 B2
APPLICATION NO. : 14/156237
DATED : August 11, 2015
INVENTOR(S) : Therasa Bell Page 1 of 1

It is certified that error appears in the above-identified patent and that said Letters Patent is hereby corrected as shown below:

Title Page, item (57) Abstract, Line 14, "HIE can" should read as --HIE in a format that allows the recipient to--

Signed and Sealed this
Seventeenth Day of May, 2016

Michelle K. Lee
*Director of the United States Patent and Trademark Office*